United States Patent
Roberts et al.

(10) Patent No.: US 7,670,287 B2
(45) Date of Patent: *Mar. 2, 2010

(54) MEDICAL DIAGNOSTIC INSTRUMENT

(75) Inventors: Chris R. Roberts, Skaneateles, NY (US); Allan I. Krauter, Skaneateles, NY (US); Michael A. Pasik, Auburn, NY (US); John R. Strom, Moravia, NY (US); Peter J. Davis, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 707 days.

This patent is subject to a terminal disclaimer.

(21) Appl. No.: 11/350,576

(22) Filed: Feb. 9, 2006

(65) Prior Publication Data

US 2006/0129031 A1   Jun. 15, 2006

Related U.S. Application Data

(62) Division of application No. 10/613,679, filed on Jul. 3, 2003, now Pat. No. 7,029,439.

(60) Provisional application No. 60/394,501, filed on Jul. 9, 2002.

(51) Int. Cl.
*A61B 1/267* (2006.01)
*A61B 1/06* (2006.01)

(52) U.S. Cl. .................. 600/200; 600/199; 600/178

(58) Field of Classification Search .................. 600/200
See application file for complete search history.

(56) References Cited

U.S. PATENT DOCUMENTS

| 715,358 | A | * | 12/1902 | Dick ........................... 72/269 |
| 1,403,659 | A | * | 1/1922 | Wadsworth ............... 200/50.18 |
| 3,373,737 | A | | 3/1968 | Moore et al. |
| 3,978,850 | A | | 9/1976 | Moore et al. |
| 4,147,163 | A | | 4/1979 | Newman et al. |
| 5,590,951 | A | * | 1/1997 | Matthews ................... 362/205 |
| 6,130,520 | A | * | 10/2000 | Wawro et al. ............... 320/114 |
| 6,383,133 | B1 | | 5/2002 | Jones |
| 2001/0002605 | A1 | * | 6/2001 | Morawski et al. ............. 156/84 |
| 2003/0029594 | A1 | * | 2/2003 | Takayanagi ................. 164/55.1 |
| 2003/0231900 | A1 | * | 12/2003 | Toriyama et al. ............ 399/159 |

FOREIGN PATENT DOCUMENTS

DE   80 07 081   6/1980

* cited by examiner

*Primary Examiner*—John P Leubecker
*Assistant Examiner*—Philip R Smith
(74) *Attorney, Agent, or Firm*—Hiscock & Barclay, LLP

(57) ABSTRACT

A medical diagnostic instrument includes a housing containing at least one battery and a light source, such as a lamp, for illuminating a medical target. A switch includes a movable member that selectively moves at least one of the battery and the lamp into and out of electrical connection with the other. The instrument is preferably fabricated from a diecast or an extrusion process wherein a thin plastic sleeve member having text and/or graphic materials can be shrink fitted onto an extruded handle.

11 Claims, 6 Drawing Sheets

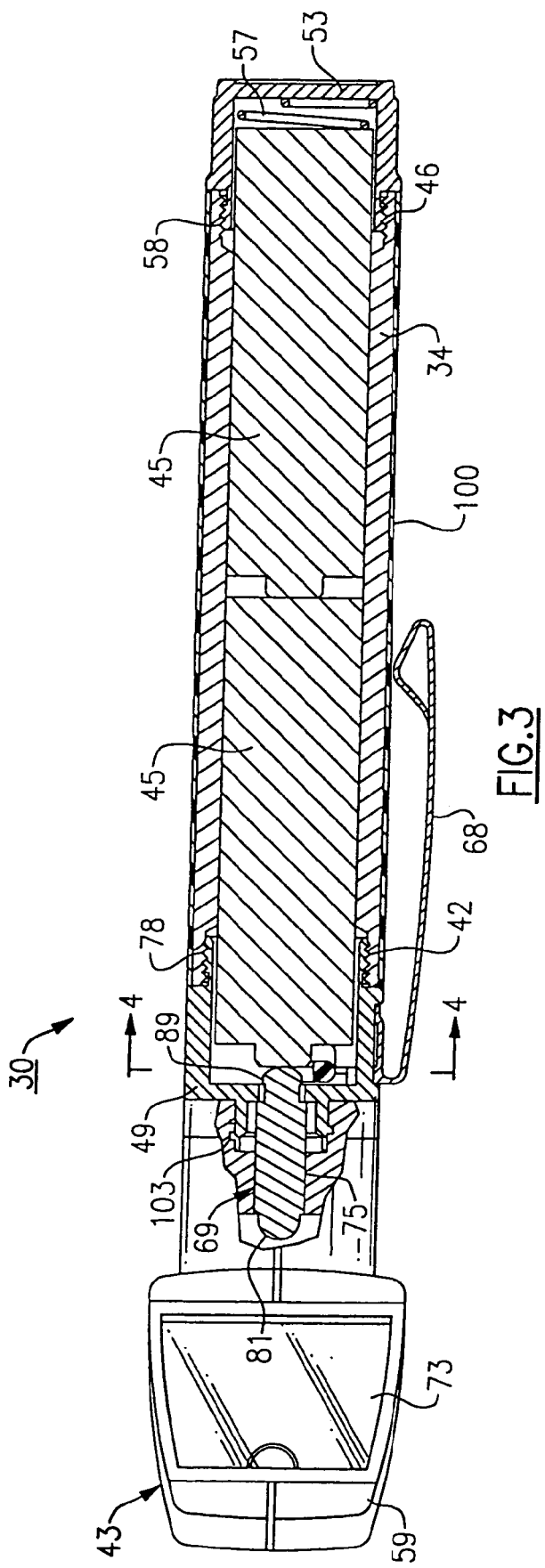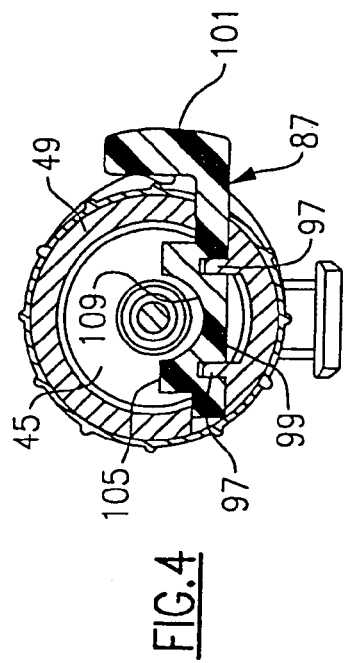

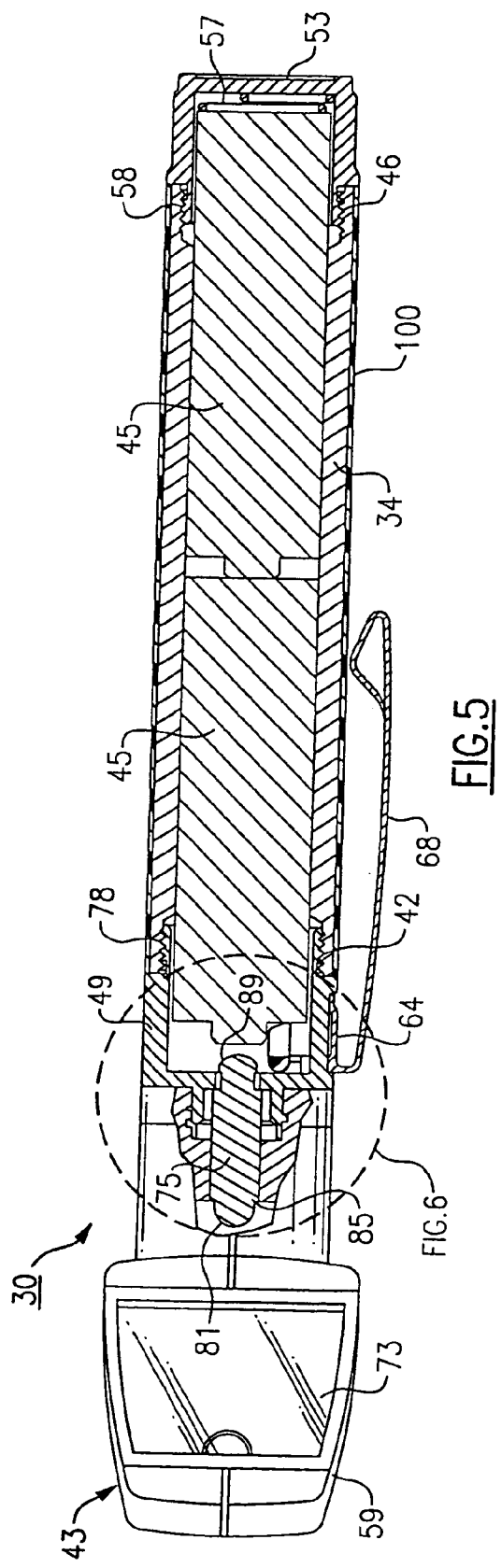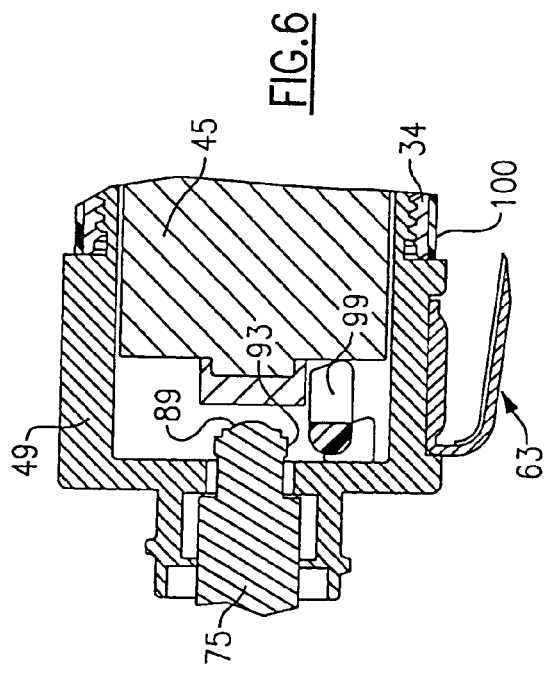

MEDICAL DIAGNOSTIC INSTRUMENT

CROSS REFERENCE TO RELATED APPLICATION

Reference is made to and priority claimed from U.S. Provisional Application Ser. No. 60/394,501 filed Jul. 9, 2002, entitled MEDICAL DIAGNOSTIC INSTRUMENT under 35 USC §119(e).

FIELD OF THE INVENTION

The present invention is directed to the field of diagnostic medicine, and in particular to a compact medical diagnostic instrument having an improved mechanical switch that provides selective electrical connection between a contained light source and at least one contained battery. Additionally, the instrument handle is made using a die-cast process wherein the handle can include a thin plastic sleeve cover member, the member being capable of having various text and/or graphic material contained thereupon.

BACKGROUND OF THE INVENTION

Currently, handles used in conjunction with compact (e.g., hand-held) diagnostic instruments, such as ophthalmoscopes and otoscopes, are based on dated designs and technologies that are at least 10 years old or more. For example, a number of known instrument designs, such as those manufactured by Welch Allyn Inc., of Skaneateles Falls, N.Y., among others, include features such as a rheostat that is provided on the instrument handle and is used to adjust illumination levels of a contained light source, such as a miniature halogen or other incandescent lamp. The latter feature adds to the complexity of the overall unit and requires a relatively large number of components to produce same, wherein it has been determined in certain settings that relatively few customers may actually use or require the benefit of the rheostat feature.

In the design of typical hand-held diagnostic medical instruments, such as ophthalmoscopes and otoscopes, a metal base or top cap is utilized. To insure the tight tolerances required for these instruments, these parts are machined from materials such as brass. Machining adds significantly to the overall cost of the instrument. It has been a goal in the field to produce a lower cost, but equally reliable diagnostic instrument. Lower cost instruments, such as those manufactured by Heine Optotechnik, Riester, and others utilize a molded plastic approach that includes a simple on/off switch. A plastic housing or handle, however, can leave customers with a perception of inferior quality.

SUMMARY OF THE INVENTION

It is therefore a primary object of the present invention to simplify the manufacture and reduce the cost of hand-held medical diagnostic instruments, such as, for example, ophthalmoscopes and otoscopes.

It is another primary object of the present invention to provide an effective, efficient means for selectively powering a compact medical diagnostic instrument with a minimum of parts being required.

Therefore and according to one preferred aspect of the present invention, there is provided a compact medical diagnostic instrument including a housing that retains at least one battery and a light source, such as a miniature incandescent lamp. The instrument further includes a switch assembly that includes a movable member that enables the at least one retained battery to selectively break electrical contact with the lamp. Preferably, the movable member of the switch assembly causes one of the at least one battery and the lamp to move relative to the other of the battery and the lamp in order to release or engage contact therewith.

According to one preferred embodiment, the movable member of the switch assembly includes a lever-type switch that includes a portion that directly engages with a set of retained batteries and causes the relative movement of the batteries vis a vis the electrical contact of the lamp assembly. Alternatively, however, other mechanical means such as wedges, cams, or rotary mechanisms can be similarly utilized for this purpose.

According to another novel aspect of the present invention is the utilization of a printed graphic sleeve member to visually enhance the look of the instrument. Most current hand-held diagnostic instruments have an external "look" that is either machined metal (e.g., smooth, knurled, etc) or plastic (ribs, smooth, etc). According to the present invention, commercial "shrink sleeves" that can incorporate multi-colored printed graphics can be added over an existing instrument handle. Images on these sleeves can include both text and graphics, covering literally any content, ranging from corporate logos to photographs, sports themes, etc. In addition, the sleeves can also include instructions for operating the instrument, wherein the sleeves can be suitably designed depending the part of the world the instrument is to be used. Preferably, the simplicity of the above design and the inclusion of the above sleeve member permits the instrument, and more particularly the instrument handle, to be made from an extrusion process that greatly simplifies the manufacturability and cost thereof.

Preferably, the top cap is made from a die cast metal, such as zinc. A zinc die cast process is similar to injection molding, in that a hard tool is created and the material is injected in a molten state to fill the tool. The result is a high tolerance, very repeatable, part. This same process can be utilized, for example, to make bases for ophthalmoscopes. To our knowledge, zinc die cast top caps (bases) are currently not utilized in diagnostic products today.

Advantages of the above mechanical switch assembly include a simple one piece construction, as in the case of the lever switch. According to one embodiment, the lever switch can be made in the form of a low cost plastic component. Obviously, fewer components results in a product that is less expensive to manufacture, in terms of both parts and labor.

The mechanical switch assembly is preferably retained in the off position, such as through the use of detents, and the assembly is configured to permit a wide range of battery sizes.

According to the present invention the design of the switch assembly creates a minimal height handle. Furthermore, the movable member of the switch assembly preferably protects the battery or batteries from shorting to the top cap of the housing in the 'ON' position when the lamp is not installed.

According to another preferred aspect of the present invention, there is provided a switch assembly for a medical diagnostic instrument, said instrument including a handle containing at least one battery and a lamp assembly including at least one electrical contact, said switch assembly including:

at least one movable member engageable with at least one of said at least one battery and said lamp assembly to move one of said at least one battery and said lamp assembly from a first position in which said electrical contact and said batteries are in electrical connection and a second position in which a spacing is formed between said battery and said electrical contact of said lamp assembly.

Advantages of a graphic art or textual sleeve member include ease in overall manufacturability and cost reduction. In addition, the sleeve members can include advertising, opaque colors or other unique features, thereby increasing versatility.

These and other objects, features and advantages will become apparent from the following Detailed Description which is to be read in conjunction with the accompanying drawings.

BRIEF DESCRIPTION OF THE DRAWINGS

FIG. 3 is a side view, taken in section, of the medical diagnostic instrument of FIGS. 1 and 2 showing a switch assembly in accordance with one aspect of the invention in a closed or "ON" position;

FIG. 4 is a partial top view of the medical diagnostic instrument of FIG. 3:

FIG. 5 is the side sectioned view of the medical diagnostic instrument showing the switch assembly of FIGS. 3 and 4 in an open or "OFF" position;

FIG. 6 is an enlarged partial view of FIG. 5;

DETAILED DESCRIPTION

Figure 1:
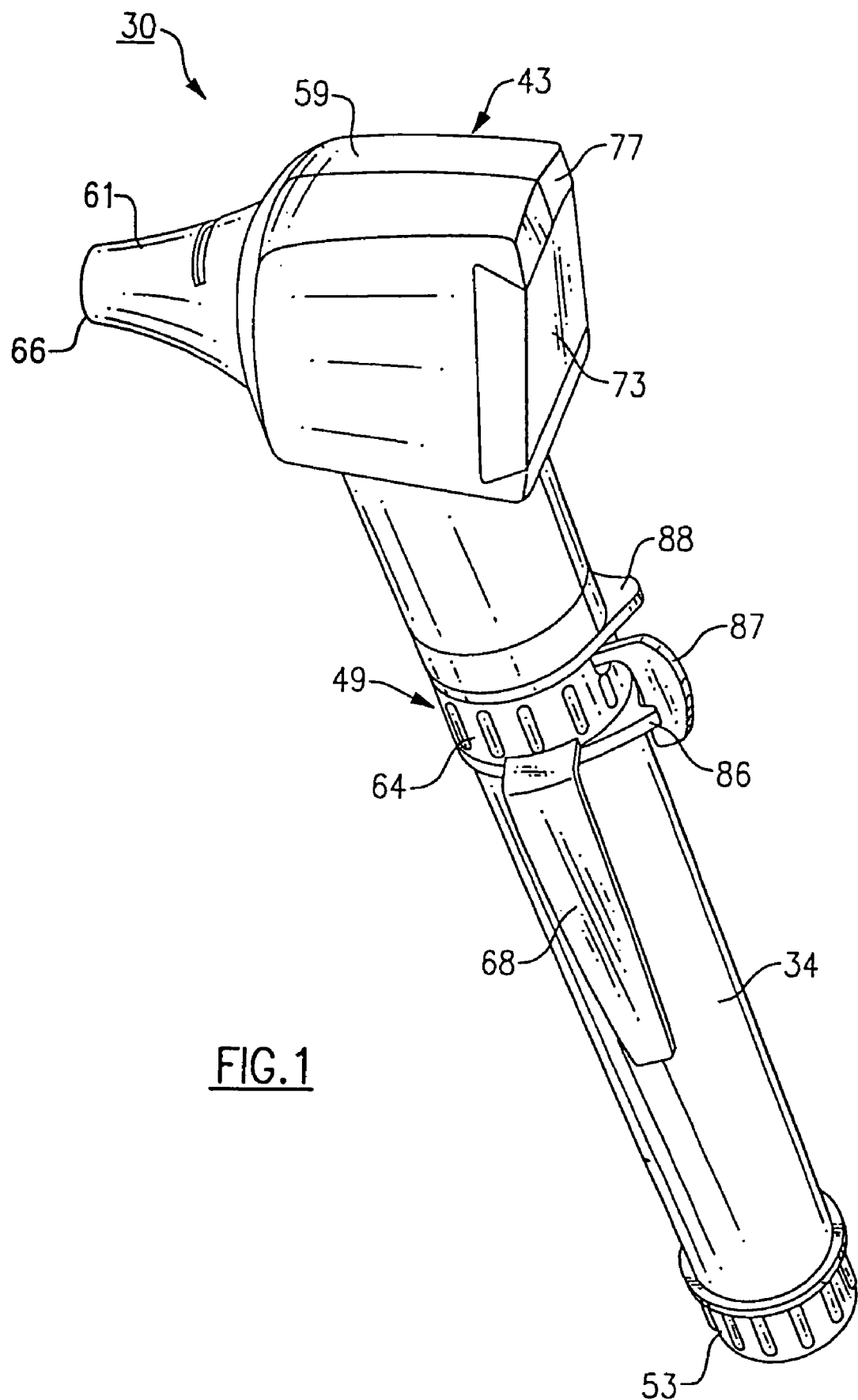
FIG. 1 is a top perspective view of a compact medical diagnostic instrument in accordance with a first preferred embodiment of the present invention.

The following description relates to certain embodiments of a medical diagnostic instrument having a mechanical switch assembly and other features as described for a specific type of instrument (e.g., an otoscope). As will become apparent from the discussion, however, the inventive concepts can easily be applied to literally any form or instrument design that includes a light source and at least one contained battery. Moreover, certain terms are used throughout the discussion, such as "top", "bottom", "above", "below", "upward", "downward", and the like that are used to provide a frame of reference with regard to the accompanying drawings. These terms, however, should not be interpreted as limiting in the sense of the scope of the invention, except where specifically indicated.

Referring to FIGS. 1-6, a compact medical diagnostic instrument is shown, herein labeled by reference numeral 30. As noted for purposes of each of the following embodiments, the herein described instrument 30 is an otoscope, used for examining the outer ear, including the tympanic membrane. The instrument 30 includes a handle 34 and an instrument head 43 that is releasably attached to the top of the handle. Preferably and according to this embodiment, the handle 34 is substantially cylindrical in shape and is defined by a hollow tubular section having a pair of open ends 37, 39 forming an interior 41 consisting of a battery compartment that is sized to retain a pair of vertically stacked batteries 45. In this embodiment and to provide better perspective in combination with the accompanying drawings, a pair of AA batteries are retained within the handle 34.

The instrument 30 further includes a top cap portion 49 and a bottom cap portion 53 sized for covering each of the open ends 37, 39, of the hollow handle 34, respectively. Preferably, each of the cap portions 49, 53 are attached by means of screw threads 78, 58 that engage with mating internal threads 42, 46 that are formed in each of the open ends 37, 39 of the tubular handle 34, respectively. The handle 34 is sized to be fitted within the palm of the hand of the intended user.

More specifically, the bottom cap portion 53 includes a compression spring 57 fitted within a defined cavity for engaging the lowermost or bottom end of the stacked batteries 45. As noted, this portion 53 includes a set of external screw threads 58 on a open distal end thereof that mate releasably with corresponding internal screw threads 46 provided on the open end 39 of the handle 34.

The top cap portion 49 of the instrument 30 is defined by a substantially hollow member having an upper mating portion 72, a lower mating portion 76 and an intermediate supporting portion 80. The intermediate supporting portion 80 includes an exterior surface 60 that receives a fitted pocket clip 63 comprising a cylindrical band 64 and a vertically extending clip member 68 that permits the compact instrument 30 to be easily carried, for example, within the shirt pocket of the user. The exterior surface 60 of the intermediate supporting portion 80 further includes a vertically extending slot 65 that is sized to accommodate a portion of a movable member 87 of a mechanical switch assembly in accordance with the invention, as described in greater detail below.

The upper mating portion 72 is a tubular cylindrical section having a diameter that is smaller than that of the remainder of the top cap portion 49, the upper mating portion further including a set of external screw threads 74. The lower mating portion 76 also includes a set of screw threads 78 and is sized to directly engage the internal screw threads 42 of the open top end 37 of the handle 34, wherein the lower mating portion is positioned within the handle when assembled thereto. Each of the top and bottom cap portions 49, 53 are made from an electrically conductive metal, such as stainless steel or preferably a die cast zinc alloy. The handle 34 is preferably made from an extruded metal such as aluminum or brass.

The instrument head 43 includes a housing 59 that includes a frusto-conical insertion portion 61 provided on a distal end that is sized for receiving a disposable speculum (not shown) permitting insertion thereof to a predetermined distance into the ear canal. The insertion portion 61 includes a distal tip opening 66 encircled with a ring of light transmitting ends (not shown) from a bundle of optical fibers (not shown), the bundle extending through the substantially hollow exterior of the instrument head in proximity to a contained lamp assembly 69 installed at the base of the head 43. The head 43 further includes a magnifying eyepiece 73 that is mounted on a proximal end 77 along a defined optical path aligned with the distal tip opening 66. An opening (not shown) is also defined in one of the sides of the instrument head 43 for inclusion of a pneumatic or other pressurized source (not shown) for insufflation of a patient's ear during examination. It should be noted that the overall design and features of the otoscopic instrument head, as described in this paragraph, are commonly known to those in the field and require no further discussion, except where needed, in regard to the present invention.

The lamp assembly 69, FIG. 3, is defined by an assembly housing 75 made from a conductive material, such as brass or stainless steel, and contains a light source 81 in the form of a miniature incandescent lamp 81 positioned within a defined cavity 85, FIG. 5, thereof. The lamp assembly 69 further includes an electrical contact 89 at a proximal end 93 thereof. Such lamp assemblies are described, for example, in U.S. Pat. No. 4,147,163, and are commonly known, the assemblies themselves not forming an essential part of the invention. Alternatively, other types of miniature light sources are within the intended scope of the invention, including LEDs.

In this embodiment, the lamp assembly 69 is fixedly attached to the base of the instrument head 43 in a vertical orientation, such that the electrical contact 89 projects downwardly therefrom and the glass envelope of the lamp is positioned at the top extending from the distal end of the assembly housing 75. The instrument head 43 further includes a set of internal screw threads 103 that engage with the external screw threads 74 provided on the upper mating portion 72 of the top cap portion 49, permitting releasable assembly thereto. When fully assembled, a through opening of the top cap portion 49 permits the top (e.g., the cathode) of the contained batteries 45 to make electrical contact with the extending electrical contact 89 of the lamp assembly 69. As previously noted, the contained batteries 45 are biased into contact with the electrical contact 89 of the lamp assembly 69 by means of the compression spring 57 located in the bottom cap portion 53. In passing, it should be noted that the lamp assembly 69, though described as being part of the instrument head 43, could alternately could be attached directly to the top cap portion 49.

As shown in FIGS. 4 and 6, the mechanical switch assembly according to this embodiment, consists of the movable member 87. Preferably, the movable member 87 is fabricated from a non-conductive material such as plastic that is made via a low cost manufacturing process, such as injection molding. The movable member 87 is installed through the slot 65 formed in the intermediate supporting portion 80 of the top cap portion 49. The slot 65 is then substantially covered and the movable member 87 is effectively retained by the cylindrical band 64 of the pocket clip 63. The portion 99 of the movable member 87 extending into the top cap portion 49 is pivotally attached therein and is retained, by means of ribs 97.

The movable member 87 further includes an extending or exterior lever portion 101 that can be rotated between a first OFF position and a second ON position by the user. Preferably, the top cap portion 49 includes a pair of stop plates 86, 88, FIG. 1, to prevent overrotation of the movable member 87 in either direction by the user, the stop plates being arranged relative to the exterior lever portion 101. The portion 99 of the movable member 87 extending into the top cap portion 49 includes a flap 105, the flap having a center cutout or recess 109 for avoiding the battery contact. In addition, detent features are provided such that the movable member 87 can be secured in the off position, as shown more particularly in FIGS. 9 and 10. Preferably, the lower stop plate 86 includes a pocket 110 at the predetermined end of travel of the movable member, the pocket being defined by a downwardly ramped surface 114 extending into a retaining surface 117. The exterior lever portion 101 includes a beveled surface 121 that permits release of the movable member 87 from the defined pocket 110 of the stop plate 86 upon sufficient finger force by the user. In addition, a beveled surface 125 is also similarly provided on the leading edge of the flap 105 for creating an overcenter engagement with the top of the stacked batteries 45, FIG. 2.

The threads of the instrument head 43 and the mating top cap portion 49 are preferably designed in terms of their overall length and pitch such that, when assembled, the insertion portion 61 is juxtaposed relative to the movable member 87. That is, the eyepiece 73, in the case of the otoscopic head, is directly above the exterior lever portion 101 of the movable member 87.

Figure 9:
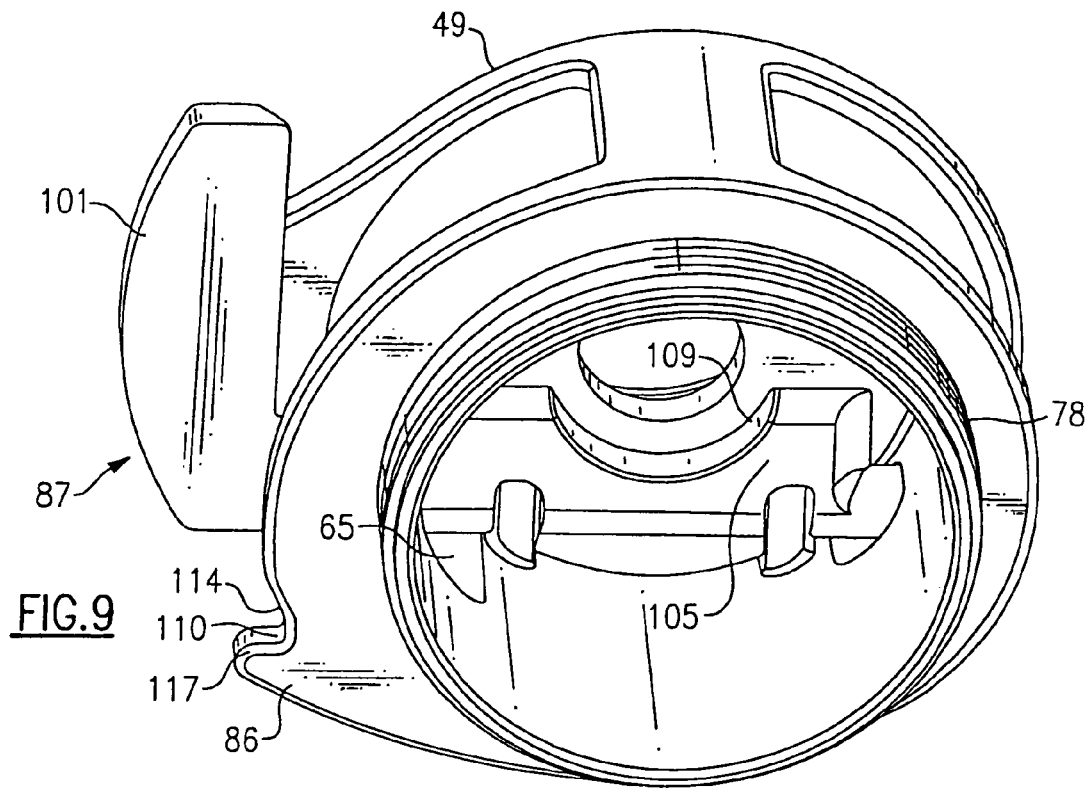
FIGS. 9 and 10 are partial bottom perspective views of a top cap portion of the instrument of FIGS. 1-6, FIG. 9 showing the switch assembly in the "ON" position, and FIG. 10 showing the switch assembly in the "OFF" position.

In operation, the lamp is energized when the exterior lever portion 101 is in the ON position of FIGS. 3, 4 and 9 in which the electrical contact 89 of the lamp assembly 69 is in electrical connection with the top of the batteries 45. The compression spring 57 provides sufficient biasing force for the circuit to be completed, wherein the instrument handle 34 is made from a conductive material, such as metal, as it provides a continuous path for the electricity to flow. The use of the compression spring 57 as described herein also compensates for small differences between battery lengths without impacting performance.

Figure 2:
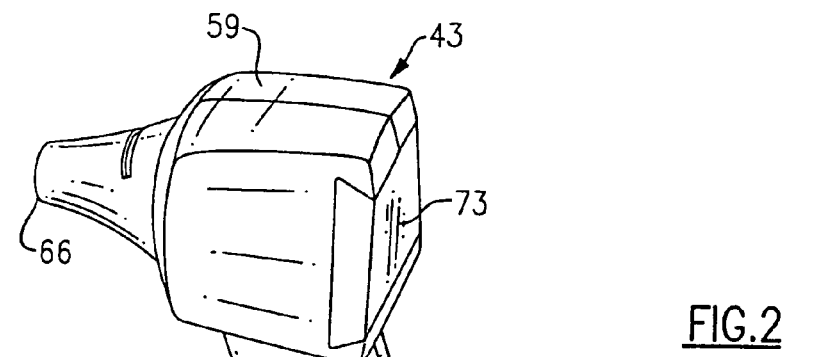
FIG. 2 is an exploded view of the medical diagnostic instrument of FIG. 1.
Figure 10:
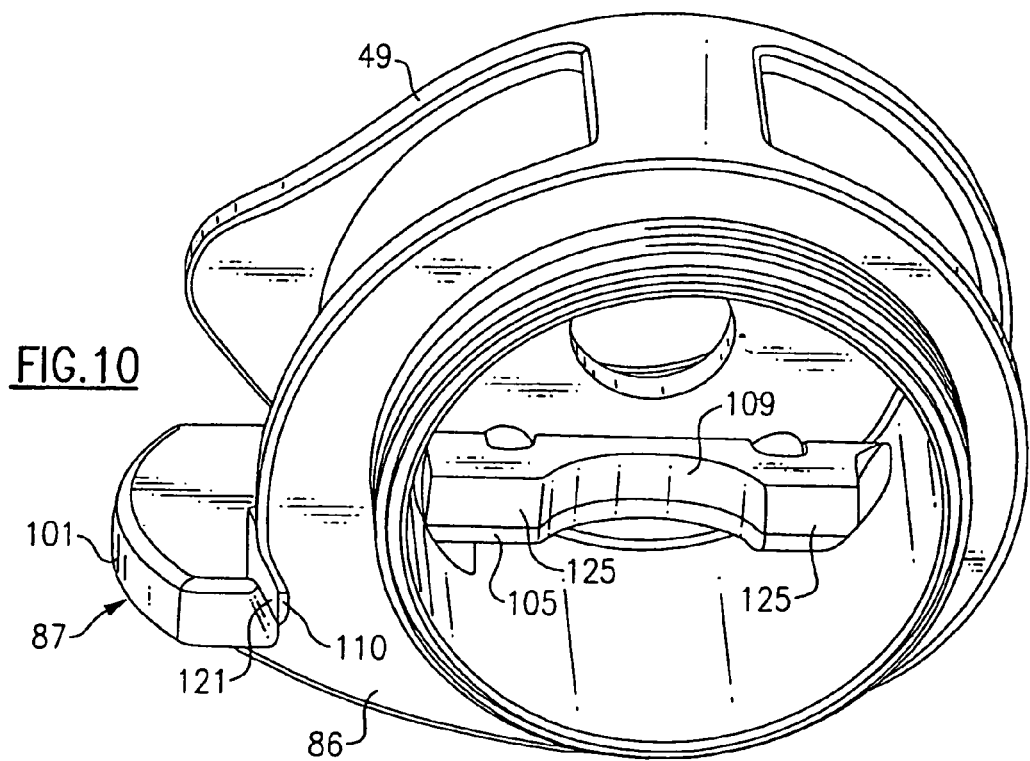

Rotation of the exterior lever portion 101 of the movable member 87, in this instance, using a clockwise direction by the user, as shown by arrows 102, FIG. 2, causes the engagement end 99 to pivot and causes the flap 105 to push the stacked batteries 45 against the biasing force supplied by the compression spring 57 and thereby creates a gap between the batteries 45 and the electrical contact 89 at the proximal end of the assembly housing 75, as shown most clearly in FIGS. 5, 6 and 10. As noted above, the exterior lever portion 101 is drawn over the stop plate 86 and into the defined pocket 110, wherein the ramped surface 114 provided a detent, thereby securing the movable member in this position. In the meantime, the beveled surface 125 at the leading edge of the flap 105 also creates positive engagement with the top of the batteries 45. In this OFF position for the instrument 30, as shown in FIGS. 5 and 6, the battery contact is disconnected directly from the electrical contact 89 of the lamp assembly 69.

Typically known hand-held diagnostic instruments utilize a metal top cap. To insure the tight tolerances, this part is machined from a material such as brass. The handle of the instrument is also typically made from brass, preferably plated machined brass. Because of the relative lack of complexity afforded the instrument of the present invention, these components can be fabricated using a metal die cast process (for the top cap) or extruded aluminum (for the handle), thereby providing a substantial cost reduction. The metal die cast process is similar to injection molding, in that a hard tool is created and the material is injected in a molten state in order to fill the tool. The resulting product is a high tolerance, very repeatable part. This same process can be utilized to make parts for any other diagnostic instrument utilizing the present invention. To our knowledge, metal die cast bases are currently not utilized in diagnostic products today.

Referring to FIG. 2, another novel aspect of the present invention includes the utilization of a printed plastic graphic sleeve member 100 to visually enhance the look of the instrument 30. Most products today have an external "look" of machined metal (smooth, knurled, etc) or plastic (ribs, smooth, etc). A proposed solution to this problem is to use commercial "shrink sleeves" that can incorporate multi-colored printed graphics. Images can include both text and graphics, covering literally any content, ranging from corporate logos, photographs, sports themes, etc. It is believed this has never been done on any medical diagnostic product(s). In addition, the sleeve member can also include instructions for operating the switch assembly, wherein the instructions or other information can be written in any language, thereby customizing the instrument for use anywhere in the world.

Figure 7:
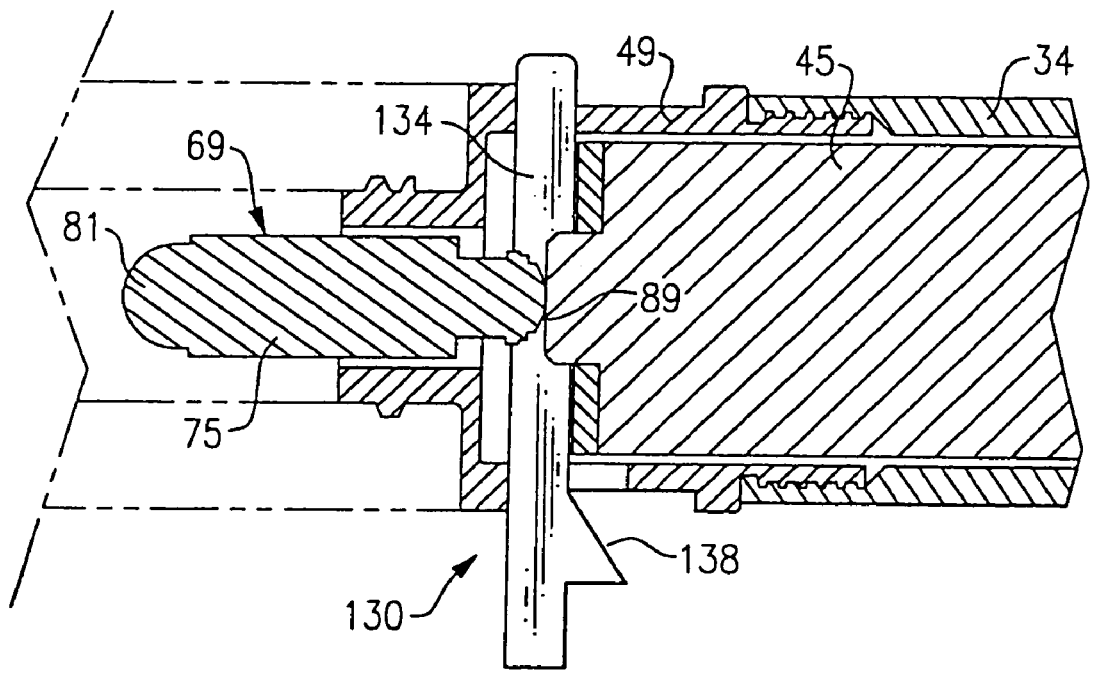
FIG. 7 is a side sectioned view of a compact medical diagnostic instrument having a switch assembly in accordance with a second preferred embodiment of the present invention, the switch assembly being shown in a closed or "ON" position.
Figure 8:
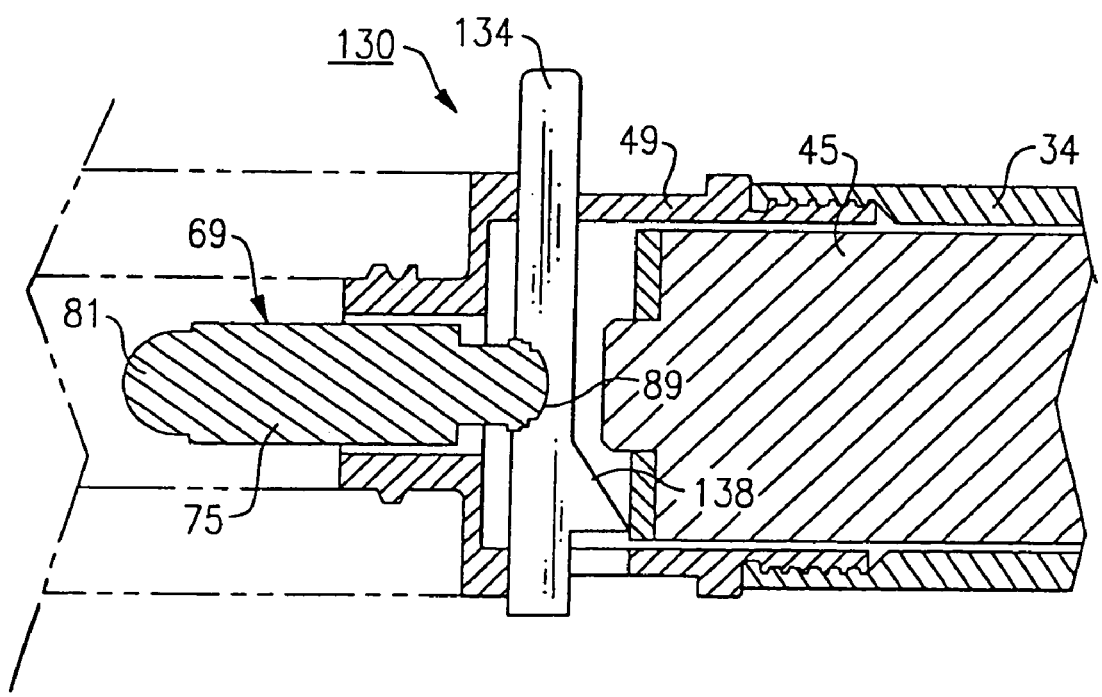
FIG. 8 is a side sectioned view of the medical diagnostic instrument of FIG. 7, with the switch assembly being shown in the open or "OFF" position.

A number of alternative embodiments to the switch assembly 83 of FIGS. 1-6 are conceivable. Examples of such embodiments are herein briefly described:

As shown in FIGS. 7 and 8, a mechanical switch assembly 130 in accordance with a second preferred embodiment of the present invention is herein described. For purposes of clarity, those features that are substantially similar to those of the preceding embodiment are labeled with the same reference numerals. In this example, a diagnostic instrument similarly includes a substantially cylindrical hollow handle 34 and an instrument head 43, as in the preceding, wherein a pair of batteries 45 are retained within the interior 41 of the hollow handle 34. A lamp assembly 69 is positioned relative to the top of the handle 34 or as in this embodiment is fixedly disposed in the bottom of the instrument head 43.

The switch assembly 130 according to this embodiment includes a movable pin-like member 134 having an angled wedge portion or section 138 at one end. The pin-like movable member 134 is movable within aligned openings that are provided in the top cap portion 49 in a direction that is substantially perpendicular to the vertical or battery axis of the instrument.

According to this embodiment, one end of the movable member 134 extends from the exterior of the top cap portion 49 of the handle 34 and is accessible by the user, wherein the angled wedge section 138 can selectively be interposed between the top surface of the upper or topmost battery 45 and the lamp electrical contact 89, thereby creating respective ON and OFF positions. Preferably, the angled wedge section 138 is insulated electrically. As in the preceding and in the absence of the angled wedge section, the biasing force of the compression spring 57 is sufficient to create necessary engagement between the electrical contact 89 of the lamp assembly 69 and the batteries 45. Features similar to the detent features described in the preceding embodiment can be added to insure positive engagement in one or both of the on and off positions.

As noted, the preceding are examples of switch assemblies and it is anticipated that other similar approaches could be contemplated for moving one or both of the batteries and/or the lamp assembly.

Moreover, it should be pointed out that the location of the herein described switch assembly can easily be varied. For example, a lever or other movable element (not shown) made in accordance with the inventive concepts discussed herein could be alternatively be provided that breaks the electrical connection at the bottom of the instrument handle. Furthermore, all movements described herein have related to those of the batteries. It should be readily apparent that similar mechanisms could be developed for moving the lamp assembly in lieu of the batteries to selectively break electrical contact or that each of the batteries and the lamp assembly can be made movable relative to one another.

As noted, the preceding instrument included an otoscopic instrument head, but other instrument heads can be similarly attached to the handle 34. For example, an ophthalmoscopic head (not shown) can be attached in lieu of an otoscopic head. As noted, the preceding are examples of switch assemblies and it is anticipated that other similar approaches could be contemplated for moving one or both of the batteries and/or the lamp assembly.

PARTS LIST FOR FIGS. 1-10

30 medical diagnostic instrument
34 handle
37 open end
39 open end
41 interior
42 screw threads, handle
43 instrument head
45 vertically stacked batteries
46 screw threads, handle
49 top cap portion
53 bottom cap portion
57 compression spring
58 screw threads, bottom cap portion
59 housing
60 exterior surface
61 frusto-conical insertion portion
63 pocket clip
64 cylindrical band
65 slot
66 distal tip opening
68 clip member
69 lamp assembly
72 upper mating portion
73 eyepiece
74 screw threads
75 assembly housing
76 lower mating portion
77 proximal end
78 screw threads, top cap portion
80 intermediate supporting portion
81 light source
85 cavity
86 stop plate
87 movable member
88 stop plate
89 electrical contact
93 proximal end
97 ribs
99 extending portion
100 plastic sleeve member
101 exterior lever portion
102 arrows
103 internal screw threads
105 flap
109 cutout or recess
110 pocket
111 projecting portion
114 ramped surface
117 retaining surface
121 beveled surface
125 beveled surface
130 switch assembly
134 movable member
138 angled wedge section While the present invention has been particularly shown and described with reference to the preferred mode as illustrated in the drawings, it will be understood by one skilled in the art that various changes in detail may be effected therein without departing from the spirit and scope of the invention as defined by the following claims.

We claim:

1. A handheld diagnostic instrument comprising:
a handle having at least one retained battery;
an instrument head releasably attached to said handle;
a light source assembly contained within said handle, said light source assembly having a stationary electrical contact in proximity to said at least one retained battery wherein said at least one battery is biased into said stationary electrical contact of said light source assembly in a first position;
a switch assembly having a movable member extending from said handle that when moved, overcomes said bias and moves said at least one battery from said first position to define a spacing in order to permit selective energization and de-energization of said light source assembly; and at least one plastic sleeve member attached over the exterior of said handle, said handle further being made using a low-grade manufacturing process and said sleeve member including at least one of a graphic and a textual symbol.

2. A diagnostic instrument as recited in claim 1, wherein said handle is made from a conductive material.

3. A diagnostic instrument as recited in claim 2, wherein said handle is made using an extrusion process.

4. A diagnostic instrument as recited in claim 1, including a top cap interconnecting said instrument head and said handle, said top cap being made using a metal die cast process.

5. A diagnostic instrument as recited in claim 1, wherein said at least one sleeve member is shrink-fitted onto said handle.

6. A diagnostic instrument as recited in claim 1, wherein said at least one sleeve member includes printed instructions for using said instrument.

7. A method for fabricating a low-cost diagnostic instrument, said instrument including a handle, an instrument head, and a base interconnecting said instrument head to said handle, said method including the steps of:

fabricating said handle from a low-grade manufacturing process, said handle being made from an electrically conductive material;

disposing a light source in said instrument and interconnecting said light source to a stationary electrical contact;

disposing at least one battery in said handle for powering said light source;

disposing a switch assembly in relation to said light source and said at least one battery, said switch assembly including a movable member extending from said handle, which when engaged, causes said at least one battery to be axially shifted in relation to said stationary electrical contact for selectively powering said light source;

applying a thin plastic sleeve member onto the exterior of said fabricated handle; and adding at least one graphic and textual symbol to said sleeve member.

8. A method as recited in claim 7, including the additional step of fabricating said base from a metal die cast process.

9. A method as recited in claim 7, including the additional step of fabricating said base from a metal die cast process.

10. A method as recited in claim 9, wherein said at least one graphic and textual symbol includes printed instructions for operating said instrument.

11. A method as recited in claim 7, wherein said base is made from a zinc alloy.

* * * * *